(12) United States Patent
Hagura et al.

(10) Patent No.: US 7,501,136 B2
(45) Date of Patent: Mar. 10, 2009

(54) DEODORANT COMPOSITION

(75) Inventors: Toyoki Hagura, Tokyo (JP); Akira Fuji, Tokyo (JP); Shunichi Akiba, Tochigi (JP); Hiroshi Kusuoku, Tochigi (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 10/949,252

(22) Filed: Sep. 27, 2004

(65) Prior Publication Data
US 2005/0100520 A1 May 12, 2005

(30) Foreign Application Priority Data

| Sep. 30, 2003 | (JP) | ............................. 2003-342371 |
| Sep. 30, 2003 | (JP) | ............................. 2003-342372 |
| Sep. 30, 2003 | (JP) | ............................. 2003-342374 |

(51) Int. Cl.
*A61K 36/756* (2006.01)
(52) U.S. Cl. ...................... 424/725; 514/560
(58) Field of Classification Search ........................ None
See application file for complete search history.

(56) References Cited

U.S. PATENT DOCUMENTS

| 1,353,916 | A | 9/1920 | Knopf |
| 5,593,683 | A | 1/1997 | Viegas et al. |
| 6,488,919 | B1 | 12/2002 | Murphy et al. |
| 6,719,966 | B2* | 4/2004 | Abrutyn ....................... 424/65 |
| 2003/0003068 | A1* | 1/2003 | Mayes et al. ................. 424/66 |
| 2003/0202949 | A1 | 10/2003 | Abrutyn |
| 2005/0100520 | A1 | 5/2005 | Hagura et al. |
| 2005/0142085 | A1 | 6/2005 | Takeuchi et al. |
| 2006/0029553 | A1 | 2/2006 | Fuji et al. |

FOREIGN PATENT DOCUMENTS

| JP | 47-003847 | 2/1972 |
| JP | 5-262633 | 10/1983 |
| JP | 60-58909 | 4/1985 |
| JP | 62-038101 | 2/1987 |
| JP | 1-128934 | 5/1989 |
| JP | 5-39215 | 2/1993 |
| JP | 7-118132 | 5/1995 |
| JP | 9-30931 | 2/1997 |
| JP | 11-29455 | 2/1999 |
| JP | 11-302151 | 11/1999 |
| JP | 2000-191511 | 7/2000 |
| JP | 2000-256156 | 9/2000 |
| JP | 2000-256345 | 9/2000 |
| JP | 2001-139444 | 5/2001 |
| JP | 2001-226213 | 8/2001 |
| JP | 2001-302482 | 10/2001 |
| JP | 2002-47190 | 2/2002 |
| JP | 2002-68954 | 3/2002 |
| JP | 2002-145793 | 5/2002 |
| JP | 2002-255776 | 9/2002 |
| JP | 2003-26527 | 1/2003 |
| JP | 2003-81700 | 3/2003 |
| JP | 2003-095843 | 4/2003 |
| JP | 2003-95907 | 4/2003 |
| JP | 2003-113013 | 4/2003 |
| JP | 2004-307396 | 11/2004 |
| KR | 2003-0043302 | 6/2003 |

OTHER PUBLICATIONS

Stuhlfauth et al. (Biochemical Systematics and Ecology (1985), vol. 13, No. 4, pp. 447-454).*
Patent Abstracts of Japan, JP 2002-255776, Sep. 11, 2002.
Patent Abstracts of Japan, JP 01-016713, Jan. 20, 1989.
Patent Abstracts of Japan, JP-2003-292427, Oct. 15, 2003.
Internet Article 'Online!, "Herbal Deodorant 2.5", XP-002311369, Dec. 17, 2004.
Karl Laden, Antiperspirants and Deodorants, Marcel Dekker INC., 1999, pp. 248-249.
U.S. Appl. No. 10/550,858, filed Sep. 26, 2005, Akiba et al.
Federal Register, 68, No. 110, pp. 34273 et seq—2003.

* cited by examiner

*Primary Examiner*—Susan C Hoffman
(74) *Attorney, Agent, or Firm*—Oblon, Spivak, McClelland, Maier & Neustadt, P.C.

(57) ABSTRACT

Provided is a deodorant composition containing (A) an extract of a plant selected from phellodendron (*Phellodendron amurense* or *P. chinensis*), ginkgo (*Ginkgo biloba*), *Lithospermum erythrorhizon*, licorice (*Glycyrrhiza glabra*) and gardenia (*Gardenia jasminoides*), and (B) an unsaturated fatty acid. This deodorant composition has benefits such as an excellent deodorant effect and even if it contains powder, it does not leave substantially any white residue on the skin.

14 Claims, No Drawings

DEODORANT COMPOSITION

FIELD OF THE INVENTION

The present invention relates to a deodorant composition having an excellent deodorant effect.

BACKGROUND OF THE INVENTION

Antiperspirant deodorants exhibit their deodorant effect by utilizing an antiperspirant or a bactericide contained therein, but those having a sufficient deodorant effect are still desirable.

There have been attempts to attain a higher deodorant effect, for example, by improving the anti-perspiration performance of an antiperspirant (Japanese Patent Publication No. 2002-523347-A=WO 2000/010521), by adding a metal oxide for deodorization (Japanese Patent Publication No. 217169/1986-A), or by incorporating a large amount of a bactericide.

From the biological viewpoint, however, perspiration cannot be stopped completely. Addition of a metal oxide is not effective for complete deodorization, because it cannot be applied uniformly to the skin surface due to its nature of being a powder. The bactericide is added desirably in a small amount in consideration of its influence on the human body and burden on the environment.

Deodorants containing powder for improving the skin feel involves a problem that after their application, a white residue remains on the skin and it deteriorates the appearance.

SUMMARY OF THE INVENTION

The present invention provides a deodorant composition containing (A) an extract of a plant selected from phellodendron (*Phellodendron amurense* or *P. chinensis*), ginkgo (*Ginkgo biloba*), *Lithospermum erythrorhizon*, licorice (*Glycyrrhiza glabra*) and gardenia (*Gardenia jasminoides*), and (B) an unsaturated fatty acid.

DETAILED DESCRIPTION OF THE INVENTION

The present invention relates to a deodorant composition having benefits such as an excellent deodorant effect and substantially not leaving a white residue on the skin after application.

The present inventors have found that a deodorant composition, having benefits such as an excellent deodorant effect and substantially not leaving a white residue on the skin even if it contains a powder, can be obtained by using a specific plant extract and an unsaturated fatty acid in combination.

The plant extract to be used in the invention is an extract of a plant selected from phellodendron, ginkgo, *Lithospermum erythrorhizon*, licorice and gardenia.

Of these plant extracts, the phellodendron extract is known to have a bactericidal action (for example, Japanese Patent Publication Nos. 2001-226213-A and 2003-113013-A), but its effect may be lower than that of conventional bactericides. For example, the MIC (Minimum Inhibitory Concentration) of the phellodendron extract against *Staphylococcus aureus* is from 0.15 to 2.5%, while that of isopropyl methylphenol which is a widely used bactericide is 0.015% (Clinical Microbiology, 26(2), 219(1999)).

The preferred plant extract to be used in the invention has an inhibitory action against degradation, by a microorganism, of Apolipoprotein D, which is a carrier protein of an odor molecule, on the skin surface. A better deodorant effect is available by using the plant extract having such an action in combination with an unsaturated fatty acid.

The plant to be used as a base of Component (A) in the invention is selected from phellodendron, ginkgo, *Lithospermum erythrorhizon*, licorice and gardenia.

The whole plant or a portion thereof such as leaf, root, rhizome, fruit, seed and flower may be used as is or after pulverization. The portion preferably employed as the plant is the bark of phellodendron, leaf of ginkgo, root of *Lithospermum erythrorhizon*, root of licorice and fruit of gardenia.

The term "extract" as used herein means an extract in a solvent available by extracting the plant in a proper solvent at normal temperature or under heating, or extracting the plant by using an extraction tool such as a Soxhlet extractor; or a diluted solution, concentrate or dry powder of those extracts. The extract may be a mixture obtained from two or more of the above-described plants.

Examples of the solvent used for extraction include water; alcohols such as methanol, ethanol, propanol and butanol; polyhydric alcohols such as propylene glycol and butylene glycol; ketones such as acetone and methyl ethyl ketone; esters such as methyl acetate and ethyl acetate; linear or cyclic ethers such as tetrahydrofuran and diethyl ether; halogenated hydrocarbons such as dichloromethane, chloroform and carbon tetrachloride; hydrocarbons such as hexane, cyclohexane and petroleum ether; aromatic hydrocarbons such as benzene and toluene; polyethylene glycol having an average molecular weight of from 180 to 1000; pyridine; ester oils such as isopropyl myristate and isopropyl stearate; oils and fats such as olive oil and diacylglycerol; and supercritical carbon dioxide. These solvents may be used either singly or in combination.

When ethanol is used, a water-ethanol mixture is preferred. The mixture preferably has an ethanol content of 50 v/v % or greater, more preferably 80 v/v % or greater, even more preferably 95 v/v % or greater.

The extracting conditions may differ depending on the solvent to be used. When a water-ethanol mixture is used, for example, 10 g of the plant is extracted with from 70 to 150 mL of the solvent at from 15 to 35° C., preferably from 20 to 25° C. for from 30 hours to 10 days, preferably from 5 to 8 days.

In the invention, it is preferred to use a hydrophobic fraction of the plant extract, that is, a fraction obtained by extracting the plant or extract thereof with a hydrophobic solvent. Examples of the hydrophobic solvent used here include esters such as methyl acetate and ethyl acetate; ethers such as diethyl ether; halogenated hydrocarbons such as dichloromethane, chloroform and carbon tetrachloride; hydrocarbons such as hexane, cyclohexane, petroleum ether and squalane; aromatic hydrocarbons such as benzene and toluene; supercritical carbon dioxide; ester oils such as isopropyl myristate and isopropyl stearate; oils and fats such as olive oil and diacylglycerol; and silicone oil. They may be used either singly or in combination. Of these, use of supercritical carbon dioxide or hexane is preferred.

Inactive impurities may be removed from the extract by liquid-liquid distribution technology or the like. In the present invention, the extract is preferably used after removal of the impurities and, if necessary, after further deodorization or discoloration by a known manner.

The extract may be used as is or in a diluted or concentrated form, or as a powder or paste form by concentrating or freeze-drying the extract.

Component (A) is incorporated in the whole composition preferably in an amount of from 0.0001 to 5 wt. %, more preferably from 0.0005 to 2 wt. % in terms of solid content.

As the unsaturated fatty acid used as Component (B) in the invention, those having from 14 to 18 carbon atoms are preferred. Examples include myristoleic acid, cis-6-hexadecenoic acid, cis-9-hexadecenoic acid (palmitoleic acid), oleic acid, linoleic acid and linolenic acid.

As Component (B), the above-described fatty acids may be used singly or in combination. Its content in the whole composition is preferably from 0.001 to 5 wt. %, more preferably from 0.005 to 3 wt. %, even more preferably from 0.005 to 1 wt. %, because a deodorant effect and good skin feel can be attained at such contents.

In the invention, the solid content of Component (A) and Component (B) are used preferably at a weight ratio (A)/(B) of from 1/2000 to 10/1, more preferably from 1/200 to 5/1, because a high deodorant effect can be obtained at such a weight ratio.

The deodorant composition of the invention may further contain an antiperspirant and/or a bactericide to improve its deodorant effect.

Examples of the antiperspirant include aluminum chlorohydrate, aluminum zirconium chlorohydrate, aluminum chloride, aluminum sulfate, basic aluminum bromide, aluminum phenolsulfonic acid, and basic aluminum iodide. Its content in the whole composition is preferably from 0.1 to 30 wt. %, more preferably from 1 to 25 wt. % in order to attain comfortable skin feel and good antiperspirant effect.

Examples of the bactericide include 3,4,4-trichlorocarbanilide, triclosan, benzalkonium chloride, benzethonium chloride, alkyl trimethylammonium chloride, resorcin, phenol, sorbic acid, salicylic acid, hexachlorophene and isopropylmethylphenol. It is incorporated preferably in an amount of from 0.0001 to 1 wt. %, more preferably from 0.0005 to 0.5 wt. % in the whole composition for attaining safety and effective control of the growth of bacteria.

The antiperspirant and bactericide may be used in combination.

The deodorant composition of the invention may further contain a deodorizing powder.

Examples of the deodorizing powder include chitosan particulate, amphoteric porous particulate, zeolite, antibacterial zeolite, porous silica, zinc oxide and magnesium oxide.

As the chitosan particulate, that having an average particle size of from 0.01 to 50 μm is preferred. For example, a chitosan particulate as described in Japanese Patent Publication No. 304643/1995-A can be used.

As the amphoteric porous particulate, that having an average particle size of from 0.01 to 50 μm is preferred. For example, an amphoteric particulate as described in Japanese Patent Publication No. 316203/1995-A can be used.

As the antibacterial zeolite, zeolite having an antibacterial metal ion at its ion exchangeable portion may be used. As the antibacterial metal ion, silver, copper and zinc ions are preferred, of which silver-exchanged zeolite is more preferred. Such antibacterial zeolite can be prepared, for example, in accordance with the method described in Japanese Patent Publication No. 26955/1996-A.

As the magnesium oxide, magnesium oxide having an enhanced deodorizing effect, for example, those having a specific surface area of from 120 to 300 $m^2$/g and a pore volume of from 0.8 to 1.5 mL/g (Japanese Patent Publication No. 2001-187721-A) may be used, as well as the ordinarily employed magnesium oxide powder.

Such a powder may be used by covering therewith the surface of nylon, polyethylene, silica or the like or may be used as a composite. Examples of the composite include a composite powder (Japanese Patent Publication No. 217139/1986-A) made of a synthetic resin such as nylon, polyethylene or polypropylene and a metal oxide such as zinc oxide, magnesium oxide or calcium oxide; a composite (Japanese Patent Publication No. 2000-159602-A) of a metal such as zinc, silver or copper, or oxide thereof with a silicate; a composite powder (Japanese Patent Publication No. 2002-146238-A) containing a powder for cosmetic composition and aluminum hydroxide; a particle (Japanese Patent Publication No. 138140/1995-A) obtained by covering amorphous silica, amorphous silica-alumina, or amorphous aluminosilicate with a magnesium compound such as magnesium hydroxide, magnesium silicate or magnesium oxide; a powder (Japanese Patent Publication No. 338621/1998-A) obtained by supporting magnesium oxide in a silicic anhydride particle; and a porous powder (Japanese Patent Publication No. 2003-73249-A) obtained by combining silicon dioxide and magnesium oxide.

As the deodorizing powder, inorganic powders are preferred, with zeolite, antibacterial zeolite, porous silica, zinc oxide and magnesium oxide being more preferred.

As the deodorizing powder, the above-described powders may be used singly or in combination and is preferably contained in an amount of from 0.1 to 10 wt. %, more preferably from 0.5 to 5 wt. % in the whole composition in order to impart the composition with an excellent deodorizing effect and comfortable skin feel.

The deodorant composition of the invention may further contain a silicone powder to give a dry skin feel.

The silicone powder may be selected as needed from those usable for ordinary cosmetic compositions. Examples include methylsiloxane network polymers such as silicone rubber powder (for example, described in Japanese Patent Publication No. 243612/1990-A) and a polyorganosilsesquioxane powder (for example, in Japanese Patent Publication No. 268615/1989-A), and a crosslinked silicone/network silicone block copolymer, that is, a silicone complex powder (for example, in Japanese Patent Publication No. 196815/1995-A and Japanese Patent Publication No. 20631/1997-A) obtained by combining a silicone rubber powder and a silicone resin.

Of these, the crosslinked silicone/network silicone block copolymer is preferred, because it is effective for reducing friction, facilitates the drying of sweat and also contributes to the improvement of deodorant effect.

Commercially available products which may be used as the methylsiloxane network polymer and the crosslinked silicone/network silicone block copolymer are "KMP-590" (product of Shin-etsu Chemical) and "TOSPEARL 130 and 145" (each, product of GE Toshiba Silicones); and "KSP-100, 101, 102 and 105" (each, product of Shin-etsu Chemical), respectively.

These silicone powders preferably have an average particle size of from 0.5 to 20 μm, more preferably from 1 to 10 μm.

As the silicone powder, the above-described silicone powders may be used singly or in combination and it is incorporated preferably in an amount of from 0.1 to 20 wt. %, more preferably from 0.5 to 10 wt. % in the whole composition to attain good skin feel.

The deodorant composition of the invention may further contain a polyphenol in order to suppress the stickiness due to sweat.

The term "polyphenol" means a compound having at least two phenolic hydroxyl groups or a derivative thereof. Examples include phloroglucinol; phloroglucinol derivatives such as aspidin and aspidinol; tannin; and tannin derivatives such as pyrogallol tannin and catechol tannin.

Alternatively, crude drugs or plant extracts containing such a polyphenol can also be used.

Specific examples include tannin crude drugs obtained from mimosa, quebracho, Kusichi, gambir, *Galla Chinensis* and gallnut; and extracts from plants such as birch, rosemary (*Rosmarinum officinalis*), arnica (*Arnica Montana*), hamamelis (*Hamamelis virginiana*), Chamomile (*Chamomilla recutita*), sage (*Salvia officinalis*), St. John's bread (*Ceratonia siliqua*), henna (*Lawsonia inermis*), hop (*Humulus lupulus*), lime (*Citrus aurantifolia*), aloe (*Aloe arborescens*), wild thyme (*Thymus serpyllum*), marigold (*Calendula officinalis*), horsetail (*Equisetum arvense*), mountain gentian (*Gentiana affinis*), nettle (*Urtica dioica*), horse chestnut (*Aesculus Hippocastanum*), avocado (*Persea americana*), *Sophora angustifolia*, seaweed, milfoil (*Achillea millefolium*), coltsfoot (*Tussilago farfara*), peach (*Prunus persica*), rose, senna (*Cassia angustifolia*), thyme (*Thymus vulgaris*), white lily (*Lilium candidum*), green tea, mulberry (*Morus Alba*), Rooibos tea (*Asphalathus linealis*), Nilgiri, Pu-erh tea, pine (*Pinus sylvestris*), Japanese cedar (*Cryptomeria japonica*), hinoki cypress (*Chamaecyparis obtusa*), grape, *Aspalathus linearis*, ANSENYAKU, *Artemisia capillaris*, common mallow (*Malva sylvestris*), multiflora rose (*Rosa multiflora*), tea plant (*Camellia sinensis*), *Isodon japonicus Hara*, St John's Wort (*Hypericum perforatum*), Germanium Herb (*Geranium thunbergii*), Assam tea, comfrey (*Symphytum Officinale*), Chinese peony (*Paeonia lactiflora*), great burnet (*Sanguisorba officinalis*), white birch (*Betula papyrifera*), English ivy (*Hedera helix*), Gotu Kola (*Centella asiatica*), Tencha (powdered tea), Japanese honeysuckle (*Lonicera japonica Thunb*), loquat (*Eriobotrya japonica*), peppermint (*Mentha piperita*), strawberry saxifrage (*Saxifraga stolonifera*), *Artemisia princeps*, fennel (*Foeniculum vulgare*), white deadnettle (*Lamium album*), raspberry (*Rubus idaeus*), Japanese persimmon (*Diospyros kaki*), gentian (*Gentiana amarella*), burdock (*Arctium lappa*), hawthorn (*Crataegus monogyna*), juniper (*Juniperus communis*), perilla (*Perilla frutescens*), spearmint (*Mentha spicata*), oregano (*Origanum vulgare*), brazil wood (*Caesalpinia echinata*), wolfberry (*Lycium Chinense*) and sundew (*Drosera rotundifolia*).

Of these plant extracts, rosemary, chamomile, avocado, *Sophora angustifolia*, thyme, green tea and mulberry extracts are preferred.

The above-described extract can be obtained by extracting, with a solvent, the flower, leaf, fruit, root or stem of the corresponding plant at normal temperature or under heating in a known manner. Examples of the solvent to be used for extraction include lower alcohols such as methanol and ethanol, polar organic solvents such as propylene glycol, 1,3-butylene glycol and glycerin, and water. These solvents may be used either singly or in combination.

As the polyphenol, at least one of the above-described ones can be used and it is incorporated in the whole composition preferably in an amount of from 0.0001 to 10 wt. %, more preferably from 0.005 to 2 wt. % in terms of solid content in order to obtain higher effects.

The deodorant composition of the present invention may contain, in addition to the above-described components, components conventionally used for cosmetic compositions such as oil components, water, various surfactants, powders other than that described above, polymer compounds, humectants, antiseptics, medicinal components, perfumes and propellants.

The deodorant composition of the invention may be provided in the form of, for example, an aerosol spray, pump spray, roll-on, powder, stick or cream.

EXAMPLES

The following examples further describe and demonstrate embodiments of the present invention. The examples are given solely for the purpose of illustration and are not to be construed as limitations of the present invention.

Preparation Example 1

Preparation of Phellodendron Extract

A phellodendron extract was obtained by adding 100 mL of a 95 v/v % aqueous ethanol solution to 10 g of the bark of phellodendron and leaving the resultant mixture at room temperature for 7 days, followed by filtration (yield: 87 mL, evaporation residue: 0.72 w/v %).

Preparation Example 2

Preparation of Hydrophobic Fraction of Phellodendron

A phellodendron extract was obtained by adding 100 mL of a 95 v/v % aqueous ethanol solution to 10 g of the bark of phellodendron and leaving the resultant mixture at room temperature for 7 days, followed by filtration. After the extract was concentrated under reduced pressure, the resulting concentrate was extracted further with 100 mL of hexane, followed by filtration to obtain an extract. The extract was concentrated under reduced pressure and then dried under reduced pressure, whereby a hydrophobic fraction of phellodendron extract was obtained (yield: 0.28 g).

Preparation Example 3

Preparation of Ginkgo Extract

A ginkgo extract was obtained by adding 100 mL of a 95 v/v % aqueous ethanol solution to 10 g of the leaves of ginkgo and leaving the resultant mixture at room temperature for 7 days, followed by filtration (yield: 85 mL, evaporation residue: 1.59 w/v %).

Preparation Example 4

Preparation of *Lithospermum Erythrorhizon* Extract

An extract of *Lithospermum erythrorhizon* was obtained by adding 100 mL of hexane to 10 g of the root of *Lithospermum erythrorhizon* and leaving the resultant mixture at room temperature for 7 days, followed by filtration (yield: 84 mL, evaporation residue: 0.12 w/v %).

Preparation Example 5

Preparation of Licorice Extract

A licorice extract was obtained by adding 100 mL of a 50 v/v % aqueous ethanol solution to 10 g of the root of licorice and leaving the resultant mixture at room temperature for 7 days, followed by filtration (yield: 78 mL, evaporation residue: 3.07 w/v %).

Preparation Example 6

Preparation of Gardenia Extract

A gardenia extract was obtained by adding 100 mL of a 95 v/v % aqueous ethanol solution to 10 g of the fruit of gardenia and leaving the resultant mixture at room temperature for 7 days, followed by filtration (yield: 93 mL, evaporation residue: 1.69 w/v %).

Test 1 (Inhibitory Action Against Degradation of Apolipoprotein D)

(1) Preparation of sweat concentrate:

The armpit of each of eight males having an apocrine odor was wiped with an absorbent cotton impregnated with 1.5 mL of distilled water once a day for three days. A liquid (57.5 mL) obtained by wringing these absorbent cottons out was filtered through a filter having a pore size of 0.45 μm and then concentrated by "Centriprep YM-10" (trade name; centrifugal filter membrane produced by Millipor). Distilled water was added to the concentrate, followed by another concentration by using "Centriprep YM-10" to remove low-molecular components from the concentrate. The resulting residue was used as a sweat concentrate.

(2) To 0.04 mL of the sweat concentrate obtained by the above-described method were added 0.03 mL of a 100 mM Tris-HCl buffer, 0.02 mL of distilled water and 0.01 mL of each plant extract (obtained in Preparation Examples 1 and 3 to 6). To the resulting mixture, *Brevibacterium epiderumidis* washed three times with a 20 mM Tris-HCl buffer having a pH of 7.2 was inoculated to give a final cell concentration of about $10^8$ cfu/mL. After incubation at 37° C. for 24 hours, antibody staining was performed. For the SDS polyacrylamide electrophoresis (SDS-PAGE) gel, "Ready gels J" (trade name; product of Bio-Rad, separating gel concentration: 15%) was employed. The antibody staining was performed in the following manner. The protein separated by SDS-PAGE was electrically transferred from the gel onto a PVDF filter ("Immobilon transfer membrane", product of Millipor). After Apolipoprotein D was detected by ECL Plus Western blotting detection system (product of Amersham Pharmacia Biotech) by using an anti-Apolipoprotein D monoclonal mouse antibody (product of RDI) as a primary antibody and an HRP-labeled anti-mouse Ig antibody (product of Amersham Pharmacia Biotech) as a secondary antibody, followed by image processing, whereby the remaining ratio of Apolipoprotein D (=amount of Apolipoprotein D in a sample/amount of Apolipoprotein D in untreated sweat×100) was calculated.

As a result, when the plant extract was not added, the remaining ratio of Apolipoprotein D was 51%, while it was 85%, 81%, 82%, 72% and 80% respectively when the extracts of phellodendron, ginkgo, *Lithospermum erythrorhizon*, licorice and gardenia were added.

Apolipoprotein D was degraded and reduced in the sweat concentrate treated with *Brevibacterium epiderumidis*, but degradation of Apolipoprotein D was suppressed by the addition of a specific plant extract.

Examples 1 to 5, Comparative Examples 1 and 2

Each of the powder sprays having the composition as shown in Table 1 was prepared and evaluated for its deodorant effect and white residue on the skin. The results are shown in Table 1.

(Preparation Process)

Each of the plant extracts, oleic acid and ethanol were mixed uniformly and the resulting solution and talc were filled in an aerosol container. After clinching, LPG was compressed into it.

(Evaluation Method)

0.5 g each of powder spray was sprayed to the armpit of 10 panels having a strong armpit odor and the white residue on the skin after spraying was organoleptically evaluated in accordance with the below-described criteria. In addition, a deodorant effect eight hours after spraying was evaluated in accordance with the following criteria.

(Deodorant Effect)
Score 4: very high deodorant effect
Score 3: high deodorant effect
Score 2: relatively low deodorant effect
Score 1: low deodorant effect (White Residue on the Skin)
Score 4: no white residue remains
Score 3: a little white residue remains
Score 2: white residue remains
Score 1: white residue remains clearly An average score was calculated and the spray was judged based on the following standard.
A: average score of from 3.5 to 4.0
B: average score of from 2.5 to 3.4
C: average score of from 1.5 to 2.4
D: average score of from 1.0 to 1.4

TABLE 1

| Components (wt. %) | Examples | | | | | Comparative Examples | | |
|---|---|---|---|---|---|---|---|---|
| | 1 | 2 | 3 | 4 | 5 | 1 | 2 | 3 |
| *Phellodendron* extract (Prep. Ex. 1) | 0.5 | — | — | — | — | — | — | — |
| Hydrophobic fraction of *phellodendron* extract (Prep. Ex. 2) | — | 0.005 | — | — | — | — | — | — |
| *Ginkgo* extract (Prep. Ex. 3) | — | — | 0.5 | — | — | — | — | — |
| *Lithospermum erythrorhizon* extract (Prep. Ex. 4) | — | — | — | 0.5 | 0.5 | 0.5 | — | 0.5 |
| Oleic acid | 0.1 | 0.1 | 0.1 | 0.1 | 0.1 | — | 0.1 | — |
| Talc | 0.5 | 0.5 | 0.5 | 0.5 | — | — | — | 0.5 |
| Ethanol | 10.0 | 10.0 | 10.0 | 10.0 | 10.0 | 10.0 | 10.0 | 10.0 |
| LPG | 88.9 | 89.395 | 88.9 | 88.9 | 89.4 | 89.5 | 89.9 | 89.0 |

TABLE 1-continued

| Components (wt. %) | Examples | | | | | Comparative Examples | | |
|---|---|---|---|---|---|---|---|---|
| | 1 | 2 | 3 | 4 | 5 | 1 | 2 | 3 |
| Deodorant effect | B | A | B | B | B | C | D | C |
| White residue on the skin | A | A | A | A | — | — | — | D |

Example 6

Powder Spray

A powder spray having the following composition was prepared in a conventional manner.

| (Components) | (wt. %) |
|---|---|
| *Lithospermum erythrorhizon* extract (Prep. Ex. 4) | 3.00 |
| *Phellodendron* extract (Prep. Ex. 1) | 0.20 |
| Cis-6-hexadecenoic acid | 0.50 |
| Isopropylmethylphenol | 0.0015 |
| Isopropyl myristate | 1.50 |
| Dimethyl silicone (10 cs) | 0.02 |
| Perfume | 0.20 |
| Decamethylcyclopentasiloxane ("SH-245", product of Dow Corning Toray Silicone) | 1.5785 |
| LPG | 93.00 |

Example 7

Powder Spray

A powder spray having the following composition was prepared in a conventional manner.

| (Components) | (wt. %) |
|---|---|
| *Ginkgo* extract (Prep. Ex. 3) | 1.00 |
| Linoleic acid | 0.20 |
| Talc | 2.00 |
| Aluminum chlorohydrate ("Locron P", product of Hoechst AG) | 0.50 |
| Polyoxyethylene/methylpolysiloxane copolymer ("KF-6015", product of Shin-etsu Chemical) | 0.05 |
| Isostearyl alcohol | 0.50 |
| Perfume | 0.10 |
| Polyoxyethylene hydrogenated castor oil | 0.15 |
| Decamethylcyclopentasiloxane ("SH-245", product Of Dow Corning Toray Silicone) | 5.50 |
| LPG | 90.00 |

Example 8

Powder Spray

A powder spray having the following composition was prepared in a conventional manner.

| (Components) | (wt. %) |
|---|---|
| Hydrophobic fraction of *phellodendron* extract (Prep. Ex. 2) | 0.005 |
| Linoleic acid | 0.10 |
| Oleic acid | 0.10 |
| Aluminum chlorohydrate ("Locron P", product of Hoechst AG) | 1.00 |
| Mica | 1.50 |
| Silica | 1.00 |
| Magnesium oxide coated silica | 0.30 |
| Isopropyl palmitate | 2.20 |
| Polyoxyethylene/methylpolysiloxane copolymer ("KF-6015", product of Shin-etsu Chemical) | 0.02 |
| Isostearyl alcohol | 0.50 |
| Perfume | 0.30 |
| Decamethylcyclopentasiloxane ("SH-245", product Of Dow Corning Toray Silicone) | 0.975 |
| LPG | 92.00 |

Example 9

Powder Spray

A powder spray having the following composition was prepared in a conventional manner.

| (Components) | (wt. %) |
|---|---|
| *Ginkgo* extract (Prep. Ex. 3) | 0.20 |
| Oleic acid | 0.50 |
| Linoleic acid | 0.003 |
| Nylon powder ("Nylon powder SP-500", product of Toray) | 1.00 |
| Aluminum chlorohydrate ("REACH 101", product of REHEIS) | 2.00 |
| Silver-exchanged Zeolite | 0.10 |
| Isopropylmethylphenol | 0.002 |
| Isopropyl myristate | 1.50 |
| Dimethyl silicone (10 cs) | 0.02 |
| Perfume | 0.10 |
| Decamethylcyclopentasiloxane ("SH-245", product Of Dow Corning Toray Silicone) | 1.575 |
| LPG | 93.00 |

Example 10

Roll-On Deodorant

A roll-on deodorant having the following composition was prepared in a conventional manner.

| (Components) | (wt. %) |
|---|---|
| *Gardenia* extract (Prep. Ex. 6) | 0.20 |
| Cis-9-hexadecenoic acid | 0.20 |
| Zinc oxide coated nylon | 1.00 |
| Triclosan ("Irgasan DP-300", product of Ciba Specialty Chemicals) | 0.50 |
| Propylene glycol | 1.50 |
| Polyoxyethylene (20EO) sorbitan coconut fatty acid ester ("Rheodol TW-L120", product of Kao) | 0.25 |
| Perfume | 0.05 |
| Polyoxyethylene hydrogenated oil | 0.40 |
| Ethanol | 45.90 |
| Purified water | 50.00 |

Example 11

Roll-On Deodorant

A roll-on deodorant having the following composition was prepared in a conventional manner.

| (Components) | (wt. %) |
|---|---|
| *Phellodendron* extract (Prep. Ex. 1) | 0.30 |
| Linoleic acid | 0.30 |
| Aluminum chlorohydrate ("REACH 501 solution", product of REHEIS) | 15.00 |
| Isopropylmethylphenol | 0.02 |
| Neopentylglycol dicaprate ("Estemol N-01", product of Nisshin Oillio) | 0.10 |
| Polyoxyethylene/methylpolysiloxane copolymer ("KF-6015", product of Shin-etsu Chemical) | 0.02 |
| Perfume | 0.30 |
| Ethanol | 80.00 |
| Purified water | 3.96 |

Example 12

Pump-Spray

A pump spray having the following composition was prepared in a conventional manner.

| (Components) | (wt. %) |
|---|---|
| *Lithospermum erythrorhizon* extract (Prep. Ex. 4) | 0.50 |
| Oleic acid | 0.50 |
| Linoleic acid | 0.01 |
| Aluminum chlorohydrate ("REACH 501 solution", product of REHEIS") | 2.00 |
| Zinc oxide coated nylon | 0.20 |
| Isopropylmethylphenol | 0.20 |
| Polyoxyethylene (20EO) sorbitan coconut fatty acid ester ("Rheodol TW-L120", product of Kao) | 0.20 |
| Isopropyl myristate | 0.10 |
| Perfume | 0.20 |
| Purified water | 8.09 |
| Ethanol | 88.00 |

Example 13

Pump Spray

A pump spray having the following composition was prepared in a conventional manner.

| (Components) | (wt. %) |
|---|---|
| Licorice extract (Prep. Ex. 5) | 0.30 |
| Cis-6-hexadecenoic acid | 0.30 |
| Benzalkonium chloride ("Sanisol C", product of Kao) | 0.10 |
| Polyoxyethylene hydrogenated oil | 0.20 |
| Perfume | 0.10 |
| Purified water | 14.00 |
| Ethanol | 85.00 |

The deodorant compositions obtained in Examples 6 to 13 each had an excellent deodorant effect and they did not leave substantially any white residue on the skin regardless of the inclusion of powder.

Example 14

Powder Spray

A powder spray having the following composition was prepared in a conventional manner.

| (Component) | (Wt. %) |
|---|---|
| Hydrophobic fraction of *phellodendron* extract (Prep. Ex. 2) | 0.005 |
| Aluminum chlorohydrate ("Locron P", product of Hoechst AG) | 1.50 |
| Magnesium-oxide-coated silica | 1.00 |
| Isopropyl palmitate | 2.50 |
| Polyoxyethylene/methylpolysiloxane copolymer ("KF-6015", product of Shin-etsu Chemical) | 0.02 |
| Isostearyl alcohol | 0.50 |
| Oleic acid | 0.10 |
| Perfume | 0.30 |
| Decamethylcyclopentasiloxane ("SH-245", product of Dow Corning Toray Silicone) | 2.075 |
| LPG | 92.00 |

Example 15

Powder Spray

A powder spray having the following composition was prepared in a conventional manner.

| (Components) | (wt. %) |
| --- | --- |
| Licorice extract (Prep. Ex. 5) | 0.20 |
| Aluminum chlorohydrate ("REACH 101", product of REHEIS) | 3.00 |
| Isopropylmethylphenol | 0.0015 |
| Silver-exchanged Zeolite | 0.20 |
| Isopropyl myristate | 1.50 |
| Talc | 1.50 |
| Dimethyl silicone (10 cs) | 0.02 |
| Linoleic acid | 0.003 |
| Perfume | 0.20 |
| Decamethylcyclopentasiloxane ("SH-245", product of Dow Corning Toray Silicone) | 0.3755 |
| LPG | 93.0 |

Example 16

Pump Spray

A pump spray having the following composition was prepared in a conventional manner.

| (Components) | (wt. %) |
| --- | --- |
| *Lithospermum erythrorhizon* extract (Prep. Ex. 4) | 0.20 |
| Aluminum chlorohydrate ("REACH 501 solution", product of REHEIS) | 2.00 |
| Isopropylmethylphenol | 0.20 |
| Porous silica | 2.00 |
| Polyoxyethylene (20EO) sorbitan coconut fatty acid ester ("Rheodol TW-L120", product of Kao) | 0.20 |
| Isopropyl myristate | 0.10 |
| Zinc oxide coated nylon | 0.20 |
| Linoleic acid | 0.01 |
| Perfume | 0.20 |
| Purified water | 7.89 |
| Ethanol | 87.00 |

The deodorant compositions obtained in Examples 14 to 16 each had an excellent deodorant effect, left substantially no white residue on the skin and exhibited good stability of the powder contained in it.

Example 17

Powder Spray

A powder spray having the following composition was prepared in a conventional manner.

| (Components) | (wt. %) |
| --- | --- |
| Hydrophobic fraction of *phellodendron* extract (Prep. Ex. 2) | 0.005 |
| Crosslinked silicone/network silicone block copolymer ("KSP-105", product of Shin-etsu Chemical), an average particle size of 2 μm) | 0.5 |
| Aluminum chlorohydrate ("Locron P", product of Hoechst AG) | 1.5 |
| Isopropyl palmitate | 2.5 |
| Polyoxyethylene/methylpolysiloxane ("KF-6015", product of Shin-etsu Chemical) | 0.02 |
| Magnesium oxide coated silica | 0.5 |
| Isostearyl alcohol | 0.5 |
| Oleic acid | 0.2 |
| Perfume | 0.3 |
| Decamethylcyclopentasiloxane ("SH-245", product of Dow Corning Toray Silicone) | 3.975 |
| LPG | 90.00 |

Example 18

Powder Spray

A powder spray having the following composition was prepared in a conventional manner.

| (Components) | (wt. %) |
| --- | --- |
| *Gardenia* extract (Prep. Ex. 6) | 0.50 |
| Methylsiloxane network polymer ("KMP-590", product of Shin-etsu Chemical, average particle size; 2 μm) | 2.50 |
| Aluminum chlorohydrate ("Locron P", product of Hoechst AG) | 1.50 |
| Isopropyl palmitate | 2.50 |
| Polyoxyethylene/methylpolysiloxane ("KF-6015", product of Shin-etsu Chemical) | 0.02 |
| Magnesium oxide coated silica | 0.50 |
| Isostearyl alcohol | 0.50 |
| Oleic acid | 0.20 |
| Perfume | 0.30 |
| Decamethylcyclopentasiloxane ("SH-245", product of Dow Corning Toray Silicone) | 1.48 |
| LPG | 90.0 |

Example 19

Pump Spray

A pump spray having the following composition was prepared in a conventional manner.

| (Components) | (wt. %) |
| --- | --- |
| *Lithospermum erythrorhizon* extract (Prep. Ex. 4) | 0.20 |
| Crosslinkable silicone/network silicone block copolymer ("KSP-105", product of Shin-etsu Chemical), average particle size of 2 μm | 2.00 |
| Isopropylmethylphenol | 0.20 |
| Aluminum chlorohydrate ("REACH 501 solution", product of REHEIS) | 2.00 |
| Polyoxyethylene (20EO) sorbitan coconut fatty acid ester ("Rheodol TW-L120", product of Kao) | 0.20 |
| Isopropyl myristate | 0.10 |
| Zinc oxide coated nylon | 0.20 |
| Linoleic acid | 0.01 |
| Perfume | 0.20 |
| Purified water | 7.89 |
| Ethanol | 87.00 |

The deodorant compositions obtained in Examples 17 to 19 each had an excellent deodorant effect, gave a pleasant dry feel to the skin, did not leave substantially any white residue on the skin, and exhibited good stability of the powder contained in it.

Example 20

Powder Spray

A powder spray having the following composition was prepared in a conventional manner.

| (Components) | (wt. %) |
| --- | --- |
| Hydrophobic fraction of *phellodendron* extract (Prep. Ex. 2) | 0.005 |
| Catechol tannin | 0.10 |
| Aluminum chlorohydrate ("Locron P", product of Hoechst AG) | 1.00 |
| Silica | 1.00 |
| Magnesium oxide coated silica | 0.30 |
| Isopropyl palmitate | 2.20 |
| Polyoxyethylene/methylpolysiloxane ("KF-6015", product of Shin-etsu Chemical) | 0.02 |
| Isostearyl alcohol | 0.50 |
| Oleic acid | 0.10 |
| Perfume | 0.30 |
| Decamethylcyclopentasiloxane ("SH-245", product of Dow Corning Toray Silicone) | 2.475 |
| LPG | 92.00 |

Example 21

Powder Spray

A powder spray having the following composition was prepared in a conventional manner.

| (Components) | (wt. %) |
| --- | --- |
| *Lithospermum erythrorhizon* extract (Prep. Ex. 4) | 0.20 |
| *Sophora angustifolia* extract | 1.00 |
| Aluminum chlorohydrate ("REACH 101", product of REHEIS) | 2.00 |
| Isopropylmethylphenol | 0.0015 |
| Silver-exchanged Zeolite | 0.10 |
| Isopropyl myristate | 1.50 |
| Methylsiloxane network polymer ("KMP-590", product of Shin-etsu Chemical) | 1.50 |
| Dimethyl silicone (10 cs) | 0.02 |
| Linoleic acid | 0.0035 |
| Perfume | 0.10 |
| Decamethylcyclopentasiloxane ("SH-245", product of Dow Corning Toray Silicone") | 0.575 |
| LPG | 93.0 |

Example 22

Pump Spray

A pump spray having the following composition was prepared in a conventional manner.

| (Components) | (wt. %) |
| --- | --- |
| *Lithospermum erythrorhizon* extract (Prep. Ex. 4) | 0.50 |
| *Mulberry* extract | 0.50 |
| Isopropylmethylphenol | 0.20 |

-continued

| (Components) | (wt. %) |
| --- | --- |
| Aluminum chlorohydrate ("REACH 501 solution", Product of REHEIS) | 2.00 |
| Polyoxyethylene (20EO) sorbitan coconut fatty acid ester ("Rheodol TW-L120", product of Kao) | 0.20 |
| Isopropyl myristate | 0.10 |
| Zinc oxide coated nylon | 0.20 |
| Linoleic acid | 0.01 |
| Perfume | 0.20 |
| Purified water | 8.09 |
| Ethanol | 88.00 |

The deodorant compositions obtained in Examples 20 to 22 each had an excellent deodorant effect, did not leave substantially any white residue on the skin and exhibited good effects for suppressing stickiness due to sweat.

The invention claimed is:

1. A deodorant composition comprising:
   (A) a hydrophobic fraction of (*Phellodendron amurense*) extract,
   (B) oleic acid; and
   an antiperspirant and/or a bactericide.

2. The deodorant composition of claim 1, wherein said hydrophobic fraction of *Phellodendron amurense* extract is in an amount of 0.0001 to 5 wt. %.

3. The deodorant composition of claim 1, wherein said oleic acid is in an amount of 0.001 to 5 wt. %.

4. The deodorant composition of claim 1, wherein a solid content of hydrophobic fraction of *Phellodendron amurense* extract as Component (A) and the oleic acid as Component (B) is at a weight ratio (A)/(B) of 1/2000 to 10/1.

5. The deodorant composition of claim 1, further comprising an unsaturated fatty acid as Component (B) which is selected from the group consisting of myristoleic acid, cis-6-hexadecenoic acid, cis-9-hexadecenoic acid, linoleic acid, linolenic acid, and combinations thereof.

6. The deodorant composition of claim 1, wherein an antiperspirant is present in an amount of 0.1 to 30 wt. %.

7. The deodorant composition of claim 1, wherein a bactericide is present in an amount of 0.0001 to 1 wt. %.

8. The deodorant composition of claim 1, further comprising a polyphenol.

9. The deodorant composition of claim 1, wherein said hydrophobic fraction of *Phellodendron amurense* extract is in an amount of 0.0001 to 5 wt.% and wherein the oleic acid as Component (B) is in an amount of 0.001 to 5 wt.%.

10. The deodorant composition of claim 9, wherein said hydrophobic fraction of *Phellodendron amurense* extract is in an amount of 0.0005 to 2 wt.% and wherein the oleic acid as Component (B) is in an amount of 0.005 to 1 wt.%.

11. A deodorant composition comprising:
   (A) a hydrophobic fraction of *Phellodendron amurense* extract,
   (B) oleic acid; and
   a deodorizing powder.

12. The deodorant composition of claim 11, wherein the deodorizing powder is in an amount of 0.1 to 10 wt. %.

13. A deodorant composition comprising:
(A) a hydrophobic fraction of *Phellodendron amurense* extract,
(B) oleic acid; and
a silicone powder.

14. The deodorant composition of claim 13, wherein the silicone powder is an amount of from 0.1 to 20 wt. %.

* * * * *